United States Patent [19]

Moore

[11] Patent Number: Plant 6,254

[45] Date of Patent: Aug. 23, 1988

[54] MINIATURE ROSE PLANT NAMED MORTORCH

[75] Inventor: Ralph S. Moore, Visalia, Calif.

[73] Assignee: Sequoia Nursery, Visalia, Calif.

[21] Appl. No.: 913,089

[22] Filed: Sep. 29, 1986

[51] Int. Cl.[4] ..... A01H 5/00

[52] U.S. Cl. ..... Plt./7

[58] Field of Search ..... Plt. 7, 10

*Primary Examiner*—Robert E. Bagwill

[57] ABSTRACT

The subject of the present disclosure is a new and distinct variety of miniature rose plant characterized by orange red buds and flowers of good substance and keeping qualities.

1 Drawing Sheet

The present invention relates to a new and distinct variety of hardy, dwarf bush type rose plant of the miniature class; the variety being primarily characterized - as to novelty - by orange red buds and flowers. The general color effect being bright orange red.

The variety is further characterized by:

An abundance of bloom, with flowers, on mature plant, borne both singly and several together in loose spray or cluster.

Light fragrance.

A plant which is vigorous, of rounded, somewhat upright shape with semi-glossy to matt, small foliage with pointed leaflets; the buds and flowers being similar in form to Sheri Anne (miniature—U.S. Plant Pat. No. 3,826) but more double.

The plant, which has a normal height of 14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery, located at Visalia, Calif. under conditions of careful control and observation, as a cross between Golden Angel (miniature—U.S. Plant Pat. No. 4,028) as the seed parent and Orangeade (Floribunda—not patented) as the pollen parent.

Subsequent to origination of the variety I successfully reproduced it, at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy: dwarf; bushy; rounded — upright; seedling; greenhouse; outdoors; cut flowers; garden decoration.

Class: Miniature.

*International identification.*—Variety: Mortorch.

*Commercial synonym.*—Torch Of Liberty.

Flowers borne; Often singly but also in loose sprays of 3 to 5 or more on slender wirey stems.

Quantity of bloom: Abundant both outside and in greenhouse.

Bud:

*Peduncle.*—Rather long; slender but sturdy; erect; medium green, sometimes lightly tinted bronze (outdoors).

*Hairs.*—Numerous very fine short hairs.

*Before calyx breaks.*—Size — small. Form long; pointed with several small foliaceous appendages and numerous very small hairs on surface of bud; with foliaceous parts extending beyond the tip of the bud equal to one-half or more of its length.

*Color.*—Medium green, occasionally tinted with bronze (outdoors).

*As calyx breaks.*—Color — light orange red.

*Opening.*—Opens well in all weather.

Bloom:

*Size when fully open.*—Small, averaging about 35–40 mm (1½").

*Petalage.*—Double — averaging about 40 petals arranged regularly plus often several small petaloids.

*Form.*—High centered then becoming more rounded with petals reflexing loosely outward, and later at maturity, rolled loosely outward and downward. Open flowers may show stamens.

Petals: Fairly thick; satiny on inside and on outside surface.

*Shape.*—Outside petals, broad lanceolate (almost round); short acute tip; intermediate — broad lanceolate with short acute tip; inside — lanceolate with acute tip.

Color: Newly opened flower from a plant grown in plastic greenhouse (September 1986), Visalia, Calif.

*Outside petal.*—Outside surface — near Vermilion 18/1 but veined or shaded darker, especially near edge of petal, with near white area at petal base. Inside surface — bright red orange, near Vermilion 18 with blackish shading near petal edge; with white to yellow area at base.

*Intermediate petal.*—Outside surface similar to outside petal but with little or no dark shading. Inside surface — similar to outside petal but with little or no dark shading.

*Inner petal.*—Outside surface — similar to intermediate petal. Inside surface — similar to intermediate petal. General color effect; newly opened flowers — bright red orange. Three days open — color similar but less intense. Behavior — opens in all weather. Spent petals drop off. Flower longevity (May 1986) — plant in pot 4–5 days or longer. Cut flowers at living room temperature 4–6 days.

Reproductive organs:

*Stamens.*—Several, arranged regularly about pistils.

*Filaments.*—Varying length, medium long, light yellow.

*Anthers.*—Yellow.

*Pollen.*—Moderate amount.

*Pistils.*—Average number.

*Styles.*—Fairly even; medium length; bunched; color — reddish.

*Ovaries.*—All enclosed in calyx.

*Hips.*—Some, ball shaped, orange.

*Sepals.*—Permanent; spear shape; recurved against peduncle.

*Seed.*—Few to several.

Foliage:

*Leaves.*—Compound of five (sometimes three or seven) leaflets; fairly small; leathery; semi-glossy to matt.

*Leaflets.*—Shape: broad, lanceolate; apex acute; base rounded (sometimes acute). Margin serrate. Color: medium to dark green; new growth — normal (medium) green — sometimes reddish (outdoors). Rachis: medium strength; upperside may have a few very tiny short hairs, grooved; underside sparsely thorny (very small) with few or no tiny prickles. Stipules: short to medium length; narrow to medium width; short length; narrow points which turn out usually at about 45 degrees.

Growth:

*Habit.*—Dwarf; bushy; rounded to upright; much branched.

*Growth.*—Free vigorous; internodes short.

*Canes.*—Medium slender; sturdy.

*Main stems.*—Color: medium green.

*Thorns.*—Few to moderate amount. Prickles — none.

*Branches.*—Color: medium green. Thorns: few. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded to upright, much branched habit, substantially as illustrated and described, characterized by buds and flowers of an orange red color which is modified by darker shading and lighter areas of near white and yellow; the bud and flower resembling the variety Sheri Anne (U.S. Plant Pat. No. 3,826) in form but with more petals; and further characterized by a plant of vigorous and compact growth habit, easy to propagate from cuttings or by budding, with an abundance of small to medium size semi-glossy to matt foliage and an abundance of flowers borne both singly and in loose clusters of 3 to 5 or more.

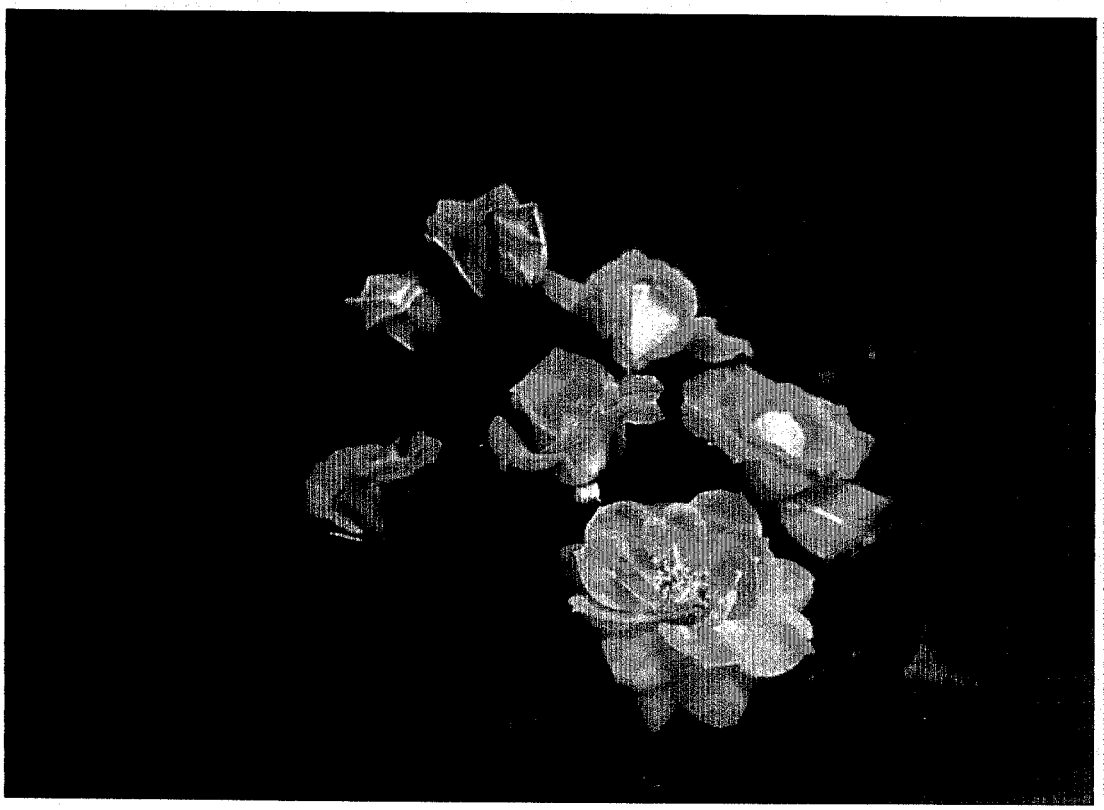

* * * * *